United States Patent
Kwon et al.

(10) Patent No.: US 9,850,482 B2
(45) Date of Patent: Dec. 26, 2017

(54) HETEROLOGOUS DNA BARCODING METHOD

(71) Applicant: Seoul National University R&DB Foundation, Seoul (KR)

(72) Inventors: Sunghoon Kwon, Seoul (KR); Junhoi Kim, Seoul (KR); Taehoon Ryu, Seoul (KR); Dongyoon Oh, Seoul (KR); Jaekyung Koh, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 78 days.

(21) Appl. No.: 14/772,914

(22) PCT Filed: Mar. 7, 2014

(86) PCT No.: PCT/KR2014/001907
§ 371 (c)(1),
(2) Date: Sep. 4, 2015

(87) PCT Pub. No.: WO2014/137193
PCT Pub. Date: Sep. 12, 2014

(65) Prior Publication Data
US 2016/0010085 A1    Jan. 14, 2016

(30) Foreign Application Priority Data

Mar. 7, 2013  (KR) ........................ 10-2013-0024355

(51) Int. Cl.
*C12N 15/10* (2006.01)
*C12Q 1/68* (2006.01)

(52) U.S. Cl.
CPC ....... *C12N 15/1065* (2013.01); *C12Q 1/6837* (2013.01)

(58) Field of Classification Search
None
See application file for complete search history.

(56) References Cited

U.S. PATENT DOCUMENTS 6,974,669 B2    12/2005    Mirkin et al.
2003/0232384 A1    12/2003    Kocher et al.

FOREIGN PATENT DOCUMENTS

WO    2006-078289 A2    7/2006

OTHER PUBLICATIONS

Meyer, M. et al., "parallel tagged sequencing on the 454 platform", Nat. Protocols, 2008, vol. 9: pp. 267-278.*
Meyer et al., "Targeted high-throughput sequencing of tagged nucleic acid samples". Nucleic Acids Research, 2007, vol. 35, No. 15, pp. 1-5.
Meyer et al., "Parallel tagged sequencing on the 454 platform". Nature Protocols, vol. 3, No. 2, 2008, pp. 267-278.
Smith et al., "Highly-multiplexed barcode sequencing: an efficient method for parallel analysis of pooled samples". Nucleic Acids Research, vol. 38, No. 13, Article No. 4142, pp. 1-7 (May 20, 2011).
International Search Report dated Jun. 12, 2014.

* cited by examiner

*Primary Examiner* — Michael Burkhart
(74) *Attorney, Agent, or Firm* — STIP Law Group, LLC

(57) ABSTRACT

A heterologous DNA barcoding method is provided. The method includes (a) providing a DNA microarray having DNA oligonucleotide spots, which are distinguished from each other by their barcode sequences, (b) providing a microwell array having microwells whose spatial arrangement corresponds to that of the DNA spots on the DNA microarray, (c) loading a solution of samples containing target nucleic acid sequences into the microwells, (d) assembling the DNA microarray to the microwell array to form micro reaction spaces in which the DNA spots are spatially separated by the microwells, (e) allowing the oligonucleotide sequences of the DNA spots to react with the target nucleic acid sequences of the samples in the micro reaction spaces to combine the sequence information of the DNA spots with the sequence information of the samples, and (f) separating the DNA microarray and the microwell array from each other to obtain reaction products including the barcode sequences.

12 Claims, 7 Drawing Sheets

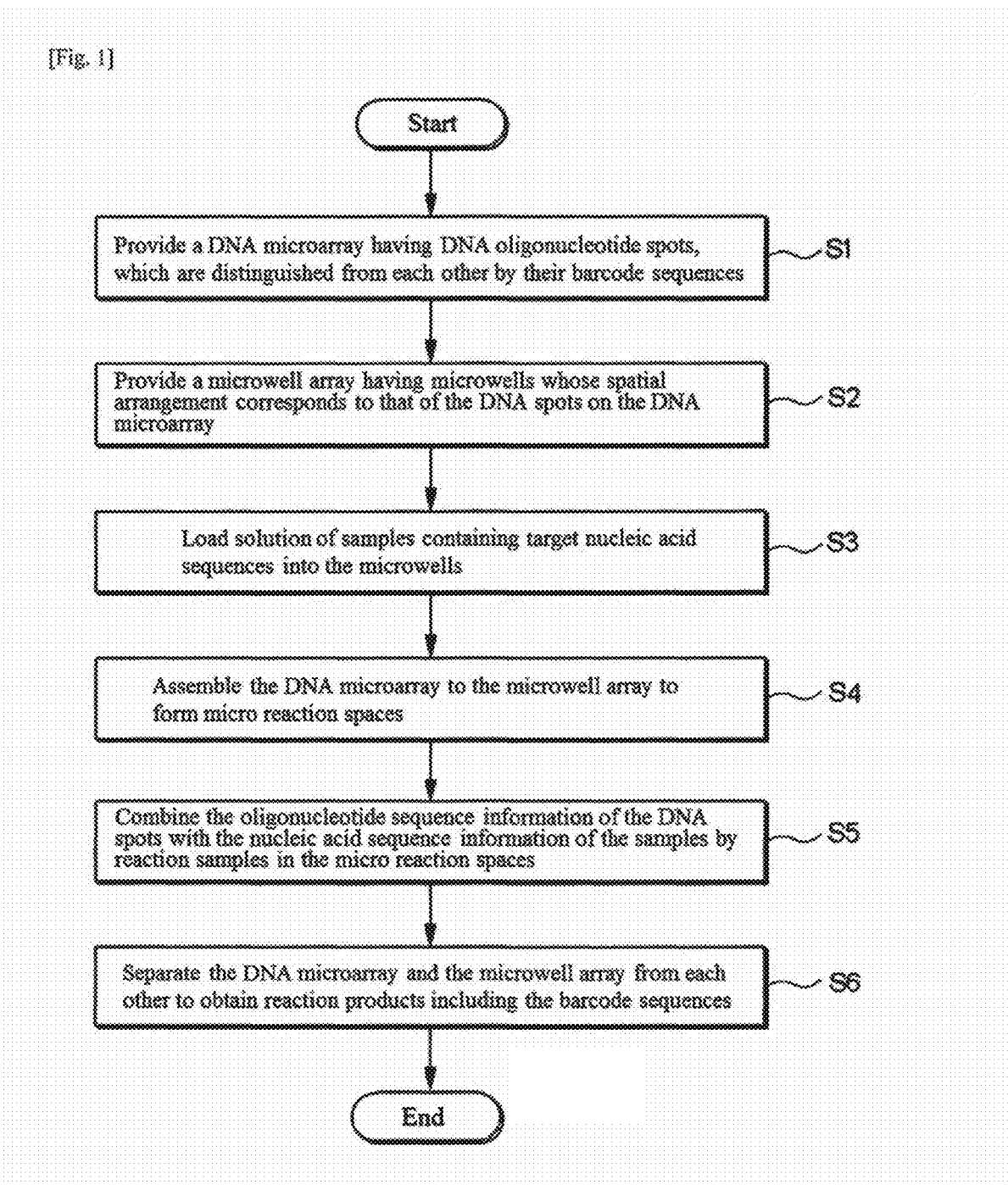
[Fig. 1]

[Fig. 2]
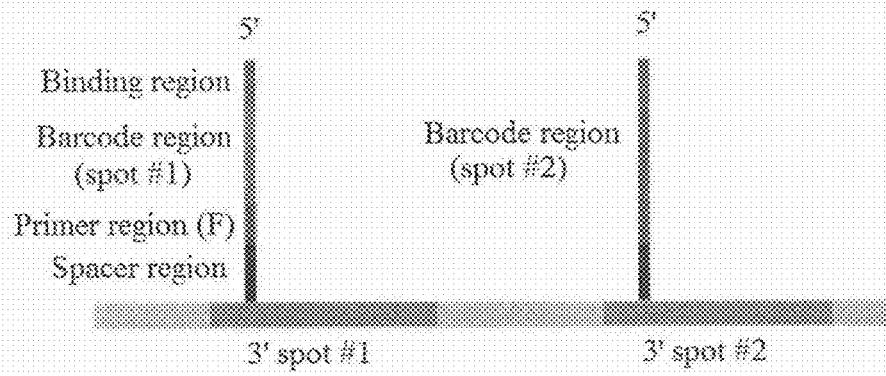
[Fig. 3]
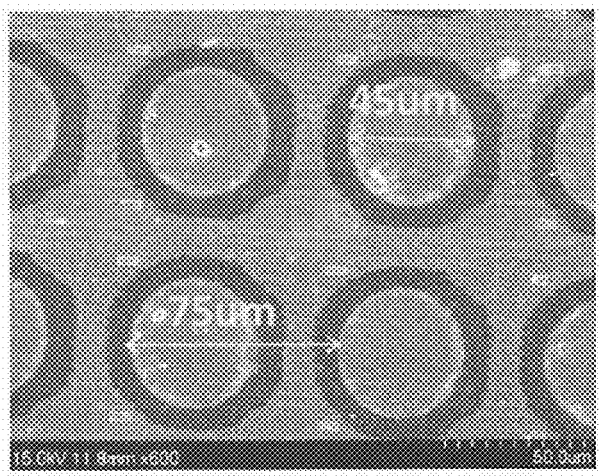
[Fig. 4]
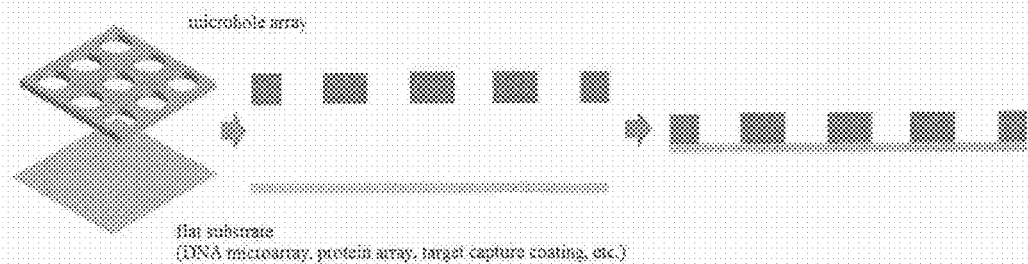

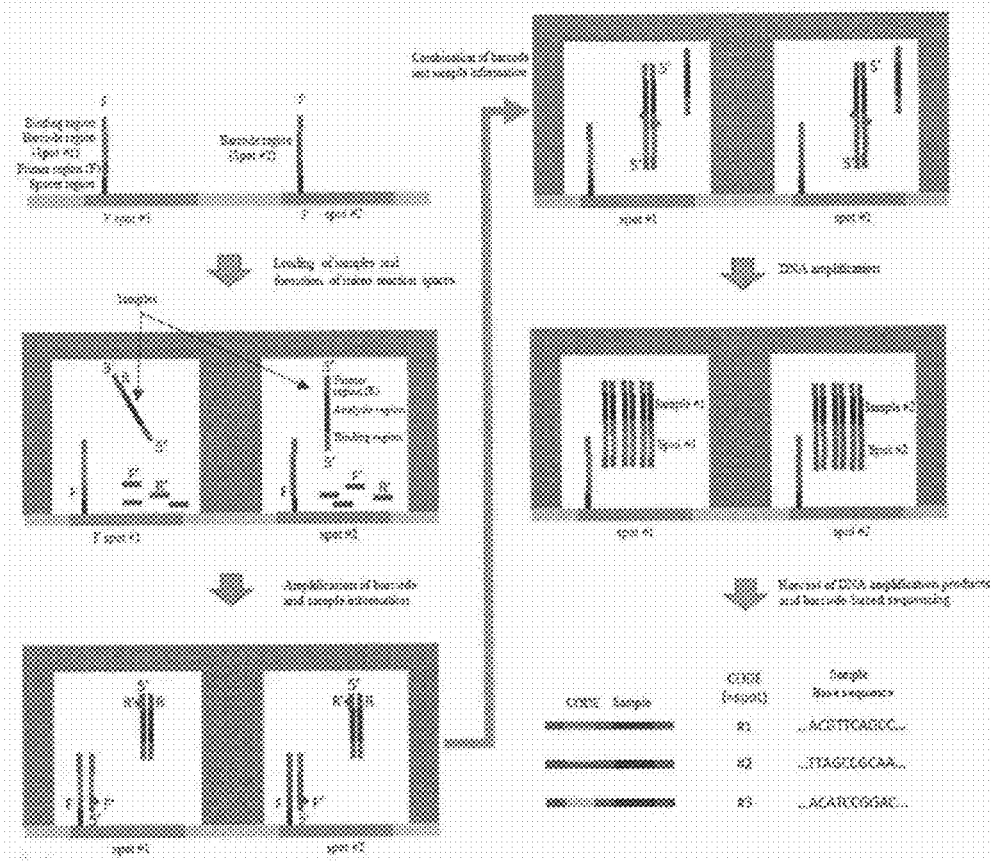

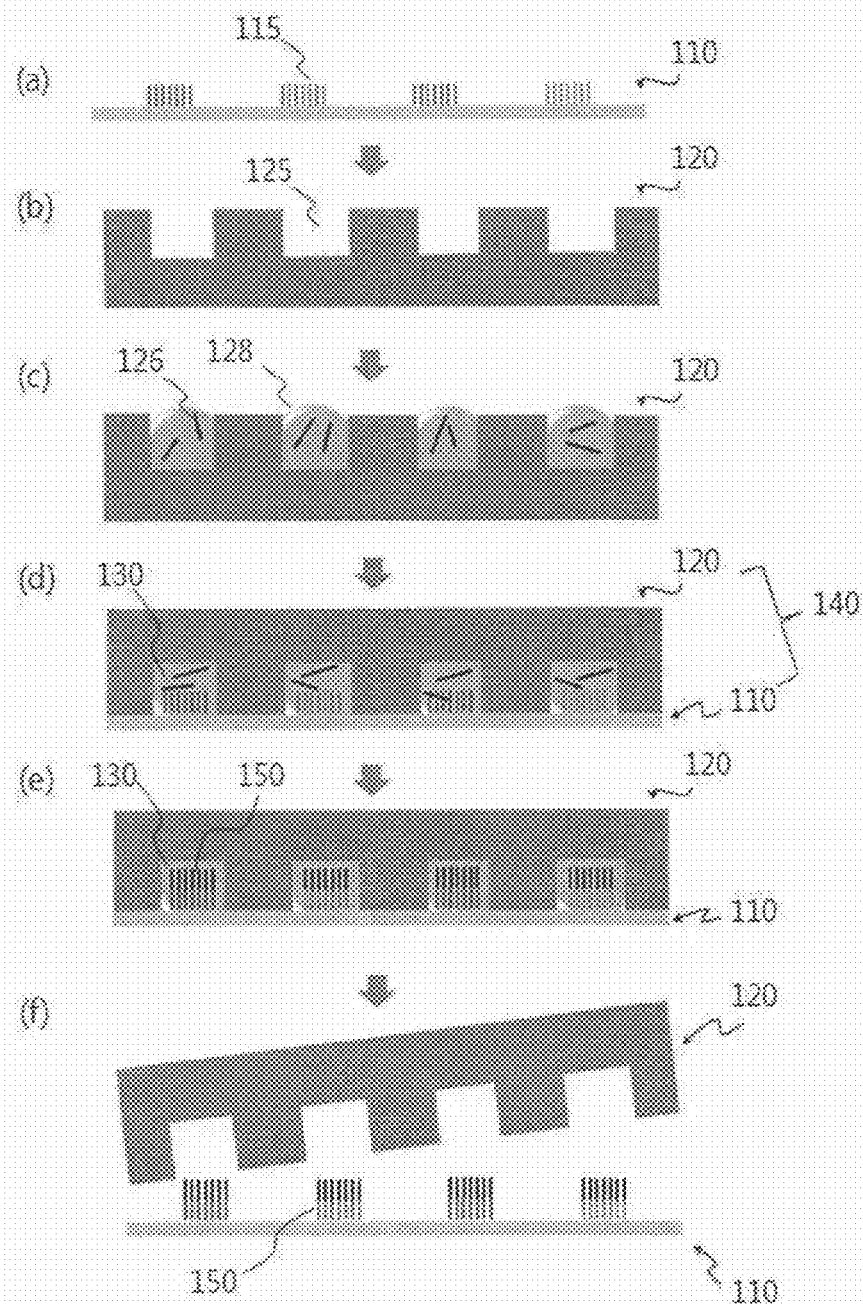

[Fig. 7]
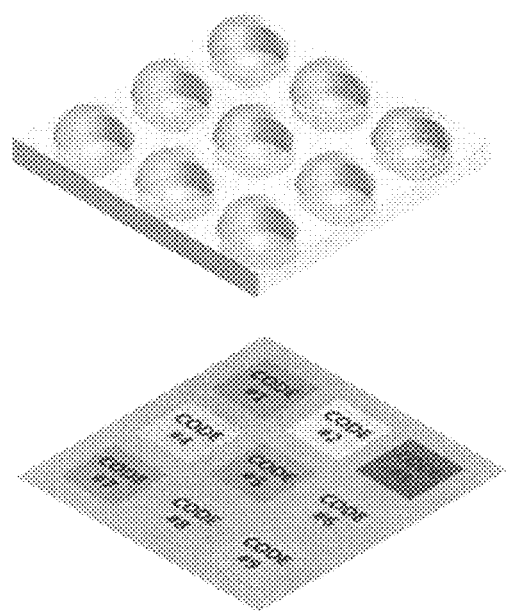

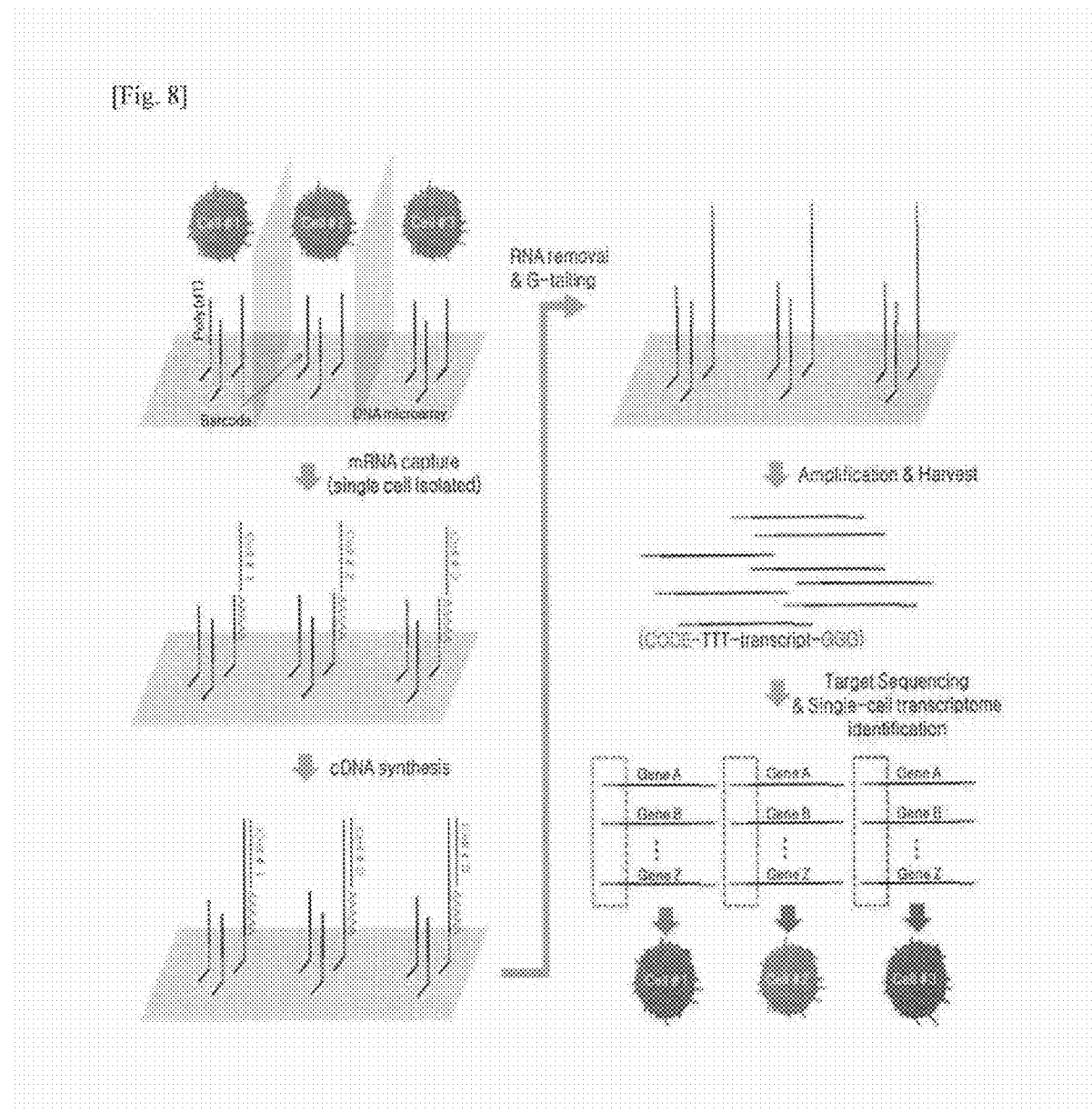

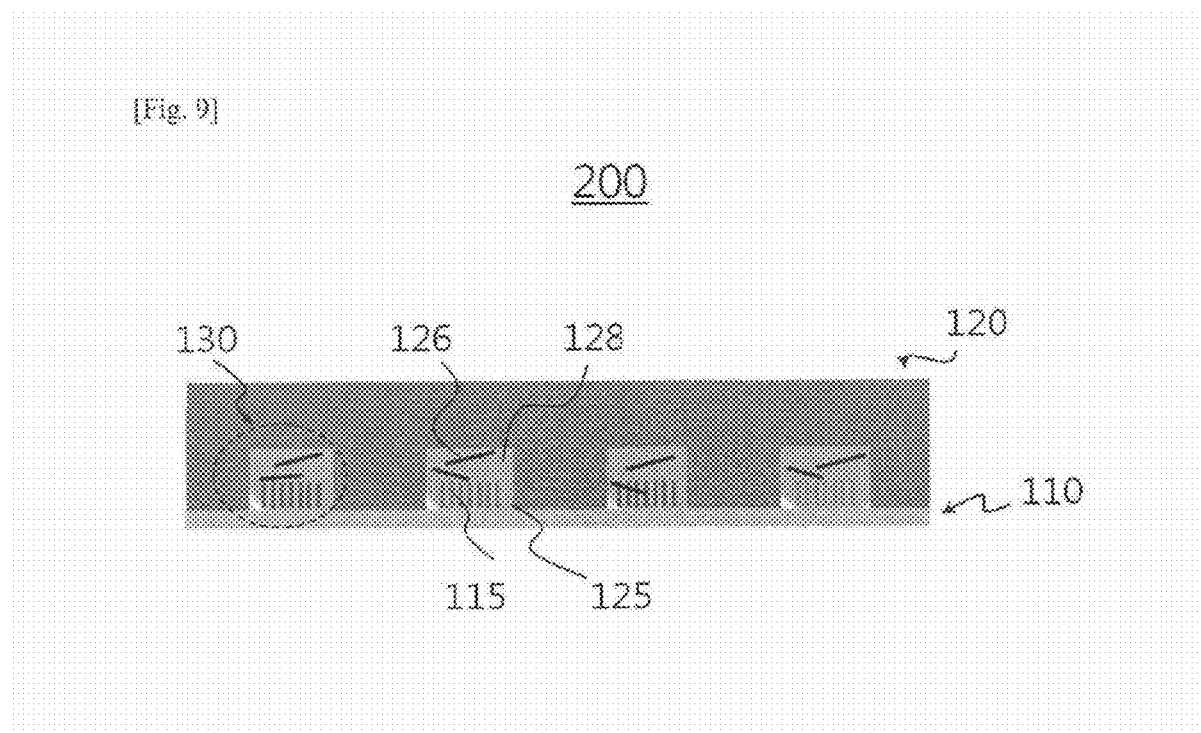
[Fig. 9]

HETEROLOGOUS DNA BARCODING METHOD

CROSS-REFERENCE TO RELATED PATENT APPLICATION

This application claims the benefit of Korean Patent Application No. 10-2013-0024355, filed on Mar. 7, 2013, in the Korean Intellectual Property Office, the disclosure of which is incorporated herein in its entirety by reference.

BACKGROUND OF THE INVENTION

Technical Field

The present disclosure relates to a heterologous DNA barcoding method, and more specifically to a heterologous DNA barcoding method for analyzing large amounts of gene samples in a simultaneous and parallel manner.

Background Art

The advent of next-generation DNA sequencing technologies has led to a dramatic increase in the number of sequences that can be read at one time. DNA barcoding based on these next-generation technologies aims at parallel reading of a great number of DNA sequences at one time. For example, Matthias Meyer and colleagues reported different methods for simultaneous analysis of two or more samples by attaching DNA barcodes to the samples by ligation (Matthias Meyer et al., Targeted high-throughput sequencing of tagged nucleic acid samples, *Nucleic Acids Research* 35, e97 (2007), Matthias Meyer et al., Parallel tagged sequencing on the 454 platform, *Nature Protocols* 3, 267-278 (2008)). Ligation of each barcode possessing an inherent sequence onto a target DNA allows for the insertion of additional information into the target DNA. Accordingly, when a large number of DNAs are analyzed, the information inherent to the barcode-tagged DNAs can also be read. For example, barcoding can be used to determine from what cells specific DNAs are extracted.

The separation and parallel analysis of different DNAs requires barcoding of the DNAs. Traditional barcoding methods necessitate the operations of constructing different DNA oligos having inherent barcode sequences and ligating the oligos to DNAs. However, traditional oligo synthesis methods entail considerable construction costs of various DNA oligos. Further, the oligos should be sequentially ligated to DNAs. This operation requires much time and labor. Large amounts of materials are also needed for the reactions, incurring considerable costs. Thus, improvements are needed.

SUMMARY OF THE INVENTION

According to one aspect of the present invention, there is provided a heterologous DNA barcoding method including (a) providing a DNA microarray having DNA oligonucleotide spots, which are distinguished from each other by their barcode sequences, (b) providing a microwell array having microwells whose spatial arrangement corresponds to that of the DNA spots on the DNA microarray, (c) loading a solution of samples containing target nucleic acid sequences into the microwells, (d) assembling the DNA microarray to the microwell array to form micro reaction spaces in which the DNA spots are spatially separated by the microwells, (e) allowing the oligonucleotide sequences of the DNA spots to react with the target nucleic acid sequences of the samples in the micro reaction spaces to combine the sequence information of the DNA spots with the sequence information of the samples, and (f) separating the DNA microarray and the microwell array from each other to obtain reaction products comprising the barcode sequences.

According to a further aspect of the present invention, there is provided a parallel DNA analysis method including (a) providing a DNA microarray having DNA oligonucleotide spots, which are distinguished from each other by their barcode sequences, (b) providing a microwell array having microwells whose spatial arrangement corresponds to that of the DNA spots on the DNA microarray, (c) loading a solution of samples containing target nucleic acid sequences into the microwells, (d) assembling the DNA microarray to the microwell array to form micro reaction spaces in which the DNA spots are spatially separated by the microwells, (e) allowing the oligonucleotide sequences of the DNA spots to react with the target nucleic acid sequences of the samples in the micro reaction spaces to combine the sequence information of the DNA spots with the sequence information of the samples, (f) separating the DNA microarray and the microwell array from each other to obtain reaction products comprising the barcode sequences, (g) sequencing the reaction products, and (h) acquiring desired samples from the reaction products by selectively amplifying the DNAs of the specific spots in the DNA microarray using the barcode information of the desired samples as a primer.

According to another aspect of the present invention, there is provided a platform for heterologous DNA barcoding comprising a DNA microarray having DNA spots, which are distinguished from each other by their barcode sequences, and a microwell array assembled to the DNA microarray and having microwells whose spatial arrangement corresponds to that of the DNA spots wherein the platform has micro reaction spaces in which the DNA spots are spatially separated from each other by the microwells and a solution of samples containing target nucleic acid sequences is loaded into the microwells in the micro reaction spaces.

BRIEF DESCRIPTION OF THE DRAWINGS

FIG. 1 is a process flow chart illustrating a heterologous DNA barcoding method according to one embodiment of the present invention.

FIG. 2 is an exemplary arrangement of DNA sequence information in spots of a DNA microarray.

FIG. 3 shows an actual image of a 12 k microarray from CustomArray.

FIG. 4 illustrates a procedure for constructing a combined microwell array using a microhole array.

FIG. 5 schematically illustrates a procedure in which DNA information of samples and barcode information are combined and amplified in micro reaction spaces.

FIG. 6 illustrates a heterologous DNA barcoding method according to one embodiment of the present invention in which samples are captured and barcoded on a DNA microarray through a series of steps (a) to (f).

FIG. 7 shows a microwell array (top) and a DNA microarray (bottom) used in a heterologous DNA barcoding method of the present invention.

FIG. 8 shows an application example of a heterologous barcoding method according to one embodiment of the present invention.

FIG. 9 is a cross-sectional diagram of a platform for heterologous DNA barcoding according to one embodiment of the present invention.

DETAILED DESCRIPTION OF THE INVENTION

Embodiments of the present invention will now be described in detail with reference to the accompanying drawings. These embodiments are provided so that this invention is thorough, and will fully convey the scope of the disclosure to those skilled in the art. Accordingly, the present invention may be embodied in many different forms and should not be construed as limited to the exemplary embodiments set forth herein. In the drawings, the dimensions, such as widths, lengths and thicknesses, of elements may be exaggerated for clarity. The same reference numerals denote the same elements throughout the drawings. The drawings are explained from an observer's point of view. It will be understood that when an element is referred to as being "on" another element, it can be directly on the other element, or one or more intervening elements may also be present therebetween.

FIG. 1 is a process flow chart illustrating a heterologous DNA barcoding method according to one embodiment of the present invention. Referring to FIG. 1, in S1, a DNA microarray having DNA spots is provided. The DNA spots are distinguished from each other by their barcode sequences. The term "DNA microarray" refers to an array of DNAs having predetermined sequences attached to portions of a solid substrate. Generally, microarrays are mostly used to measure the expression of genes from cells. When some sequences of genes whose sequences have been already known are synthesized and attached to a substrate and react with mRNAs expressed in cells, hybridization occurs between complementary sequences. At this time, fluorescence is emitted, which is measured to determine the level of expression of the genes.

In this embodiment of the present invention, the DNA microarray may be any of those that are generally used for molecular diagnosis of disease or bioinformatic analysis in the art. The DNA microarray may be a chip having a structure in which short DNA molecules (e.g., shorter than about 300 bp) having different sequences are arranged at regular intervals on a flat substrate made of glass or silicon, etc.

The DNA molecules on the DNA microarray, together with sample DNAs to be loaded in a subsequent step, participate in DNA amplification. Accordingly, it is preferred that the DNA molecules are ready for solid-phase PCR. The amplification of DNA molecules by solid-phase PCR occurs near the surface of a substrate rather than in a liquid environment, leading to deterioration of enzymatic efficiency or interference with the reaction. In an effort to suppress such adverse surface effects, the substrate is previously coated with a suitable material, such as a polymeric material, to create an environment where DNA amplification can occur or portions of the DNA molecules to be bound to the substrate are utilized as free spaces that do not participate in amplification. Alternatively, the portions of the DNA molecules other than the lengths thereof necessary for barcode amplification reaction can be utilized to provide free spaces towards the substrate.

The orientation of the DNA molecules constituting the DNA microarray may be determined depending on how to prepare the DNA molecules. For example, when the DNA microarray is constructed by photodegradation of photodegradable materials, the 3'-ends of the DNA molecules are aligned in a direction toward the substrate. Alternatively, the 5'-ends of the DNA molecules may be bound to the substrate and the 3'-ends thereof may remain free by suitable techniques, such as biochemical techniques or DNA microarray replication techniques. A printing or spotting technique may be used to bind the DNA molecules to the substrate in a desired alignment direction.

The DNA sequence information constituting each spot of the DNA microarray may include, as essential elements, (1) a binding region that recognizes and binds to sample DNA molecule to be amplified, (2) a barcode region that characterizes the corresponding spot, (3) a primer region necessary for DNA amplification, and (4) a spacer region that serves to ensure a space between the overlying regions and the underlying microwell array surface to allow for sufficient DNA amplification.

FIG. 2 is an exemplary arrangement of the DNA sequence information in the spots of the DNA microarray.

More specifically, the DNA sequence information consists of the following regions.

(1) Binding region—The same sequence information is applied to all spots and is determined depending on the sequences of target sample DNAs because it should recognize common specific sites of the sample DNA molecules.

(2) Barcode region—Different sequence information is applied to all spots such that the corresponding spot can be back traced after sequencing. Preferably, the barcode regions of the spots have different constituent sequences such that the spots are characterized by the constituent information. The barcode regions have no ability to bind to the other constituent regions of the spots, the primer sequence information, and all regions of DNA of samples to be exposed to the DNA microarray, and therefore, they are preferably designed such that there is no possibility of being bound to them. In addition, the barcode regions are preferably designed such that they do not exhibit reaction specificity depending on the constitution of the barcode sequence information even in subsequent steps of DNA amplification and sequencing after all amplified DNAs are collected together.

(3) Primer region—This region is necessary to perform DNA amplification and to acquire a DNA amplification product in which the binding region, the barcode region, and the sequence information region of a target sample are combined together. DNA amplification requires two primers in opposite directions. One of the primers is located in the sample DNA. The sequence information of the primer region is the same for all spots. If necessary, different sequence information may be inserted into the spots for selective amplification of specific spots.

(4) Spacer region—DNA amplification using the DNA microarray occurs on the microarray surface. In order to facilitate access of DNA molecules and related enzymes, insertion of the spacer region is necessary to separate the regions (1) to (3) from the microarray surface. This region does not directly participate in DNA amplification.

Referring again to FIG. 1, in S2, a microwell array is provided. The microwell array has microwells whose spatial arrangement corresponds to that of the DNA spots on the DNA microarray.

The microstructure of the microwell array is made by a semiconductor process. Reactions using the microwell array can occur in a remarkably reduced volume compared to conventional tube-based reactions. This is effective in reducing the amounts of samples and reagents necessary for the reactions and is advantageous in terms of sensitivity for confirmation of the reactions.

The size and arrangement of the microwells constituting the microwell array are determined by those of the spots constituting the DNA microarray as the counterpart. Basically, the DNA spots are arranged in a one-to-one relationship with the microwells. Alternatively, the DNA spots may be arranged in a 1:N or N:1 (where N is an integer greater than or equal to 2) relationship with the microwells. The 1:N relationship indicates that N microwells correspond to one DNA spot and the N:1 relationship indicates that N DNA spots correspond to one microwell. For example, in the case of a 12 k microarray from CustomArray including circular DNA spots, each of which has a diameter of about 45 µm, located at intervals of 75 µm in widthwise and lengthwise directions, a microwell as a counterpart to the microarray may be constructed such that microwells, each of which has a diameter of about 40 pun and a height of about 40 µm, are arranged at intervals of 75 µm in widthwise and lengthwise directions. FIG. 3 shows an actual image of the 12 k microarray from CustomArray.

The relative sizes of the microwells and the DNA spots may vary at such a level that the relationship is preserved. The height of the microwells may be determined in the range of 10% to 1000% of the diameter of the microwells depending on the type of reactions to be carried out.

Generally, the microwell array has a simple structure in which well-shaped recesses are formed on a flat substrate. Alternatively, the structure of the microwell array may be more extended. For example, a combined microwell array structure is possible in which another flat substrate is joined to a microhole array.

The flat substrate may be a DNA or protein microarray or may be coated with a biochemical substance to capture specific molecules. FIG. 4 illustrates a procedure for constructing a combined microwell array using a microhole array.

Referring back to FIG. 1, in S3, a solution of samples containing target nucleic acid sequences is loaded into the microwells. The samples, with which the barcode information derived from the DNA spots is to be combined, may be selected from:

(1) DNA or RNA molecules having one or various sequences;

(2) DNA microarrays having different oligonucleotide sequence information (e.g., a combined microwell array in which a microhole array is located between two DNA microarrays);

(3) Micro/nanoparticles including DNA or RNA molecules thereon or therein;

(4) Cells or bacteria including DNA or RNA molecules;

(5) Viral molecules including DNA or RNA molecules; and (6) DNA or RNA molecules bound to proteins.

The loading solution may include conditions of the samples and other reagents, such as enzymes and primers, for DNA binding or amplification. The samples are contained in the solution and loaded into the microwells. The number of the samples in each microwell may vary according to the objects of research to be amplified and analyzed. For example, when barcoding is carried out to quantitatively analyze the genes of single cells, the solution is prepared and loaded at an appropriate concentration of, on average, one cell per microwell. Under an assumption that the number of the samples in each microwell is consistent with a simple Poisson distribution, when the solution has a concentration of one sample per unit volume of each microwell, 37%, 37%, and 18% of the microwells include 0, 1, and 2 samples, respectively. When the solution has a concentration of 0.1 samples per unit volume of each microwell, 90%, 9%, and 0.5% of the microwells include 0, 1, and 2 samples, respectively.

The sample solution may be loaded in such a manner that it is sprayed on the microwell array chip and is allowed to naturally flow into the microwells along the hydrophilic surfaces of the microwells. Alternatively, a precision device, such as an inkjet printer or a spotter, may be used to directly load the sample solution into the microwells.

Referring again to FIG. 1, in S4, the DNA microarray is assembled to the microwell array to form micro reaction spaces in which the DNA spots are spatially separated by the microwells. The DNA microarray as a substrate is assembled to the microwell array to spatially separate and isolate the loaded sample solution and the samples in the microwell environments. The DNA microarray and the microwell array are aligned using a microscope and a stage. Alternatively, the DNA microarray and the microwell array may be designed and constructed to be automatically aligned upon assembly using a separate frame structure. After assembly, the chip consisting of the DNA microarray and the microwell array has an arrangement of a plurality of micro reaction spaces. In the micro reaction spaces, the DNA microarray spots are spatially separated by the microwells and different biochemical reactions may occur.

The micro reaction spaces may be different DNA microarray spot environments where DNA binding or amplification occurs. Therefore, the chip can serve as a platform for heterologous DNA barcoding.

Referring back to FIG. 1, in S5, the oligonucleotide sequences of the DNA spots are allowed to react with the target nucleic acid sequences of the samples in the micro reaction spaces to combine the sequence information of the DNA spots with the sequence information of the samples. In the micro reaction spaces, binding and amplification reactions (polymerase chain reaction) occur between the sample DNAs and the DNA molecules constituting the spots of the DNA microarray. Particularly, DNA amplification (solid-phase PCR) occurs near the DNA microarray surface in the early stage of the reaction due to the presence of the primer regions for DNA amplification in the spots of the DNA microarray. The DNA amplification may be performed by solid-phase PCR only or in combination with general PCR.

The combination of the DNA information of the samples with the barcode information of the DNA microarray spots can be largely achieved by the following two approaches:

(1) The sample DNA information and the barcode information are combined and amplified in one microwell environment; and (2) The combination and amplification of DNAs occurs in separate microwells. That is, the sample DNAs are preferentially combined and acquired by the DNA microarray spots in microwell environments, the microwells are separated, other microwells containing a reagent for DNA amplification are assembled, and the DNAs are amplified.

FIG. 5 schematically illustrates a procedure in which the sample DNA information and the barcode information are combined and amplified in the micro reaction spaces. As illustrated in FIG. 5, both combination and amplification occurs in one microwell environment.

In one embodiment, DNA amplification products may be obtained in which the sample DNA information is combined with the barcode information. The sample DNA information may be added to the microarray spot DNAs to extend the DNA amplification products. In an alternative embodiment, the barcode information may be ligated to the sample DNAs and may freely float in the microwells. The two embodiments are possible because the double-stranded DNAs specifically bind to complementary base sequences.

Referring again to FIG. 1, in S6, the DNA microarray and the microwell array are separated from each other to obtain reaction products including the barcode sequences.

The barcode information of the DNA microarray spots is combined with the DNA information of the samples separated by the microwells to form DNA amplification products, which can be easily obtained by disassembling the chip and harvesting the solution. The DNA amplification products are composed of different DNA molecules, in which the DNA information of the different samples is combined with the different barcodes. Therefore, the sequence information of the sample DNAs can be determined based on the barcode information after analysis of the sequences by next-generation sequencing techniques.

A further aspect of the present invention provides a parallel DNA analysis method based on the heterologous DNA barcoding. First, the products obtained in S6 are sequenced. For this sequencing, a highly parallel sequencing technique can be utilized. Examples of suitable highly parallel sequencing techniques include pyrosequencing chemistry, bridge amplification, next-generation sequencing, third-generation sequencing, next-next-generation sequencing, and semiconductor sequencing.

Desired samples can be acquired from the products by selectively amplifying the DNAs of the specific spots in the DNA microarray using the barcode information of the desired samples as a primer.

In one embodiment of the present invention, the DNAs may be selectively amplified based on the barcode information of the products. For example, when it is intended to selectively obtain desired sample DNAs after sequencing, the DNAs of the specific spots in the DNA microarray can be selectively amplified using the barcode information included in the sample DNAs as a primer.

One embodiment of a procedure for implementing the heterologous DNA barcoding method through S1 to S6 is schematically illustrated in FIG. 6. FIG. 7 shows the microwell array (top) and the DNA microarray (bottom) used in the heterologous DNA barcoding method.

FIG. 6 illustrates a heterologous DNA barcoding method according to one embodiment of the present invention. According to the method, sample are acquired and barcoded on a DNA microarray through a series of steps (a) to (f). Referring to FIG. 6, first, a DNA microarray 110 is prepared in which DNA spots 115 having barcode sequences are arranged ((a) of FIG. 6). A microwell array 120 is prepared that has microwells 125 corresponding to the DNA spots 115 ((b) of FIG. 6).

Subsequently, a solution 128 containing target gene samples 126 is loaded into the microwells 125 ((c) of FIG. 6). Examples of available gene samples 126 include animal cells, bacteria, biosubstances, such as genomes in the form of purified DNA or RNA. Other examples of the gene samples 126 include solid particles to which genes are attached. Depending on the size of the gene samples 126, the areas of the microwells 125 and the DNA spots 115 may be adjusted to several to several hundreds of micrometers. Particularly, it is essential that the locations of the microwells 125 constituting the microwell array 120 match those of the DNA spots 115 on the DNA microarray 110. For loading of the gene samples 126, the solution 128 is applied onto the microwell array 120. Predetermined amounts of the applied solution 128 enter the microwells 125 and the gene samples 126 can be evenly distributed and introduced into the wells 125. The microwells 125 are preferably constructed so as to have sizes suitable for loading of the gene samples 126.

After application of the gene samples 126 onto the microwell array 120, the DNA microarray 110 is assembled to the microwell array 120 such that they are in face-to-face contact with each other. As a result, a chip 140 is obtained in which independent micro reaction spaces 130 are arranged ((d) of FIG. 6). Since the DNA spots 115 having different barcode sequences are located in the micro reaction spaces 130, the barcodes are attached in parallel to the gene samples 126 and amplification occurs when the chip 140 is allowed to stand under particular reaction conditions, for example, PCR conditions (e.g., at 95° C. for 30 sec and at 60° C. for 60 sec, 40 cycles) after DNA hybridization at room temperature. Thus, the micro reaction spaces 130 include products 150 having the barcode information ((c) of FIG. 6). Next, the chip 140 is disassembled to acquire the products 150.

FIG. 8 shows an application example of a heterologous barcoding method according to one embodiment of the present invention. Referring to FIG. 8, cells are placed in the microwells and barcodes are attached to the genetic information of the cells to distinguish the cells based on the heterologous barcoding method. The genetic information of different cells can be distinguished using the code information after sequencing.

Another aspect of the present invention provides a platform for heterologous DNA barcoding.

FIG. 9 is a cross-sectional diagram of a platform for heterologous DNA barcoding according to one embodiment of the present invention. Referring to FIG. 9, the platform 200 includes a DNA microarray 110 having DNA spots 115, which are distinguished from each other by their barcode sequences, and a microwell array 120 coupled to the DNA microarray 110 and having microwells 125 whose spatial arrangement corresponds to that of the DNA spots 115.

The platform 200 has micro reaction spaces 130 in which the DNA spots 115 are spatially separated from each other by the microwells 125. In the micro reaction spaces 130, a solution 128 of samples 126 containing target nucleic acid sequences is loaded into the microwells 125. The solution 128 may further contain at least one substance or composition selected from the group consisting of enzymes, primers, dNTPs, surfactants for cell lysis, compositions for DNA hybridization, and buffer compositions for PCR.

When the platform 200 is allowed to stand under particular reaction conditions, such as PCR conditions, the oligonucleotide sequence information of the DNA spots 115 is combined with the nucleic acid sequence information of the samples 126 to create reaction products having the barcode sequences.

By the use of the platform of the present invention, the sequence information of the target DNA samples isolated in the different spaces defined by the microwells and the specific barcode information of the corresponding spots can be combined and amplified. Accordingly, when the amplification products are collected together and analyzed at one time in a subsequent step, the results can be analyzed based on the barcode information, and as a result, the sequence information of the samples included in the microwells can be determined.

As described above, according to the heterologous DNA barcoding method of the present invention, the DNA microarray is coupled to the microwell structure such that the sequence spots on the DNA microarray are arranged so as to correspond to the microwells. With this arrangement, independent DNA amplification reactions are obtained in the separate micro reaction spaces. Here, the sequence information of the spots of the DNA microarray is utilized as barcode information for characterizing the corresponding fine reaction spaces. That is, when independent DNA amplification reactions occur in the microwells, the sequence information of the DNA microarray spots included in the microwells is inserted in the form of barcode information into the amplification products.

According to the present disclosure, since the barcodes on the microarray can be physically separated by the microwell array, the barcodes can be attached in parallel to the samples, resulting in a considerable increase in the number of target genomic samples. The heterologous DNA barcoding method of the present invention is applicable to various scales from parallel single-cell genomic analysis to genomic analysis of tissue samples because the sizes and locations of the microwell array and the microarray can be controlled as desired. Particularly, when the heterologous DNA barcoding method of the present invention is used to analyze single-cell genomes, it is expected that cell-to-cell variability, which has been difficult to observe in conventional genomic analysis of tissues or cell masses, can be observed by simultaneous parallel analysis of a large number of samples.

The present disclosure is applicable to all forms attached to solid substrates, such as antibodies, protein arrays, and chemical arrays, and can be utilized in various fields, including protein quantification, ChIP-seq, and drug screening.

The invention claimed is:

1. A heterologous DNA barcoding method comprising (a) providing a DNA microarray having DNA oligonucleotide spots, which are distinguished from each other by their barcode sequences, (b) providing a microwell array having microwells whose spatial arrangement corresponds to that of the DNA spots on the DNA microarray, (c) loading a solution of samples containing target nucleic acid sequences into the microwells, (d) assembling the DNA microarray to the microwell array to form micro reaction spaces in which the DNA spots are spatially separated by the microwells, (e) allowing the oligonucleotide sequences of the DNA spots to react with the target nucleic acid sequences of the samples in the micro reaction spaces to combine the sequence information of the DNA spots with the sequence information of the samples, (f) separating the DNA microarray and the microwell array from each other to obtain reaction products comprising the barcode sequences, and (g) sequencing the reaction products and analyzing them based on barcode information.

2. The heterologous DNA barcoding method according to claim 1, wherein the oligonucleotide sequences constituting each DNA spot comprises i) a binding region binding to the target nucleic acid sequences, ii) a barcode region characterizing the spot, iii) a primer region for DNA amplification, and iv) a spacer region.

3. The heterologous DNA barcoding method according to claim 1, wherein the DNA spots are arranged in a 1:1, 1:N or N:1 (where N is an integer greater than or equal to 2) relationship with the microwells.

4. The heterologous DNA barcoding method according to claim 1, wherein the microwell array has a structure in which well-shaped recesses are formed on a flat substrate or a combined structure in which a flat substrate is joined to a microhole array.

5. The heterologous DNA barcoding method according to claim 1, wherein the samples are selected from (1) DNA or RNA molecules having one or various sequences, (2) DNA microarrays having different oligonucleotide sequence information, (3) Micro/nanoparticles comprising DNA or RNA molecules thereon or therein, (4) Cells or bacteria comprising DNA or RNA molecules, (5) Viral molecules comprising DNA or RNA molecules, and (6) DNA or RNA molecules bound to proteins.

6. The heterologous DNA barcoding method according to claim 1, wherein the sample solution comprises reagent conditions for DNA binding reaction and/or amplification reaction.

7. The heterologous DNA barcoding method according to claim 1, wherein, in step (e), the DNAs are amplified by solid-phase PCR.

8. The heterologous DNA barcoding method according to claim 1, wherein the oligonucleotide sequence of the DNA spots and the nucleic acid sequence of the samples are combined and amplified in one microwell environment.

9. The heterologous DNA barcoding method according to claim 1, wherein the oligonucleotide sequence of the DNA spots and the nucleic acid sequence of the samples are combined and amplified in separate microwells, and the DNAs are amplified in other microwell containing a reagent for DNA amplification after step (f).

10. A parallel DNA analysis method comprising (a) providing a DNA microarray having DNA oligonucleotide spots, which are distinguished from each other by their barcode sequences, (b) providing a microwell array having microwells whose spatial arrangement corresponds to that of the DNA spots on the DNA microarray, (c) loading a solution of samples containing target nucleic acid sequences into the microwells, (d) assembling the DNA microarray to the microwell array to form micro reaction spaces in which the DNA spots are spatially separated by the microwells, (e) allowing the oligonucleotide sequences of the DNA spots to react with the target nucleic acid sequences of the samples in the micro reaction spaces to combine the sequence information of the DNA spots with the sequence information of the samples, (f) separating the DNA microarray and the microwell array from each other to obtain reaction products comprising the barcode sequences, (g) sequencing the reaction products, and (h) acquiring desired samples from the reaction products by selectively amplifying the DNAs of the specific spots in the DNA microarray using the barcode information of the desired samples as a primer.

11. A platform for heterologous DNA barcoding comprising:
a DNA microarray having DNA spots, which are distinguished from each other by their barcode sequences;
a microwell array assembled to the DNA microarray and having microwells whose spatial arrangement corresponds to that of the DNA spots, wherein the platform has micro reaction spaces in which the DNA spots are spatially separated from each other by the microwells; and
a solution of samples containing target nucleic acid sequences, wherein the solution of samples is loaded into the microwells in the micro reaction spaces.

12. The platform according to claim 11, wherein the solution further contains at least one substance or composition selected from the group consisting of enzymes, primers, dNTPs, surfactants for cell lysis, compositions for DNA hybridization, and buffer compositions for PCR.

* * * * *